United States Patent [19]

Miller et al.

[11] Patent Number: 5,284,157
[45] Date of Patent: Feb. 8, 1994

[54] ELASTOMERIC FILM PRODUCTS WITH IMPROVED CHEMICAL RESISTANCE

[75] Inventors: Robert G. Miller, Willowdale; Oskar Tankovitz, Toronto; Duncan A. Mackillop, Etobicoke, all of Canada

[73] Assignee: Ortho Pharmaceutical Corporation, Raritan, N.J.

[21] Appl. No.: 736,369

[22] Filed: Jul. 26, 1991

[51] Int. Cl.⁵ .................................................. A61F 6/00
[52] U.S. Cl. ....................... 128/844; 128/918; 604/349
[58] Field of Search ............... 604/265, 12, 363, 292, 604/266, 347–353, 330; 427/412.1, 393.5, 2; 128/842, 844, 918, DIG. 8

[56] References Cited

U.S. PATENT DOCUMENTS

| | | | |
|---|---|---|---|
| 3,363,624 | 1/1968 | Fishman | 128/844 |
| 3,663,288 | 5/1972 | Miller | 604/266 |
| 4,479,795 | 10/1984 | Mustacich | 604/265 |
| 4,526,579 | 7/1985 | Ainpour | 604/265 |
| 4,638,790 | 1/1987 | Conway | 128/844 |
| 4,773,901 | 9/1988 | Norton | 604/265 |
| 4,829,991 | 5/1989 | Boeck | 128/844 |
| 4,919,966 | 4/1990 | Shlenker | 128/844 |
| 4,955,392 | 8/1990 | Sorkin | 128/844 |
| 4,963,623 | 10/1990 | Miller et al. | 525/237 |
| 5,039,750 | 8/1991 | Miller et al. | 525/237 |
| 5,073,365 | 12/1991 | Katz | 604/265 |
| 5,091,205 | 2/1992 | Fan | 604/265 |

OTHER PUBLICATIONS

Silkowski, et al., Permeation Through Five Commercially Available Glove Materials by Two Pentachlorophenol Formulations, Am. Ind. Hyg Assoc. J., 45(8), 501–504 (1984).

Primary Examiner—Michael A. Brown

[57] ABSTRACT

A latex film product such as a prophylactic condom, a surgical glove, a medical examination glove, and the like, having improved chemical resistance, such product comprising a shaped film consisting essentially of a cured mixture of (a) a copolymer of acrylonitrile and butadiene or isoprene, and (b) a high styrene content styrene-butadiene copolymer.

3 Claims, 1 Drawing

2

ELASTOMERIC FILM PRODUCTS WITH IMPROVED CHEMICAL RESISTANCE

The invention relates to elastomeric film products such as prophylactic condoms and surgical gloves made from certain acrylonitrile containing synthetic latexes.

BACKGROUND OF THE INVENTION

Commercial condoms have been manufactured from natural rubber (NR) latex for over sixty years. NR latex is an excellent material for the latex dipping process customarily employed for producing such articles as condoms, medical gloves, and the like, since it is stable and can readily be compounded with aqueous dispersions of curatives, e.g. sulphur, zinc oxide, preservatives etc. Also the actual dipping process is simple since a congruent film is formed on the shape former when it is dipped into the latex. Further, on the application of heat, water is rapidly evaporated and a natural rubber film of uniform thickness and integrity is formed.

It is general practice to dip the former, with the dried rubber film on it, into the latex a second time in order to minimize the presence of holes in the condom. After sulphur vulcanization by heating at 100° C. for about one hour, NR condoms exhibit high tensile strength and extensibility and good tear resistance. However since natural rubber is an unsaturated hydrocarbon elastomer, it has poor resistance to degradation by heat, light, oxygen, ozone, and bacteria. Also traces of metals, such as copper, accelerate the degradation.

Natural rubber is also readily swollen, weakened, and degraded by contact with chemical fluids, in particular by hydrocarbon oils and solvents. It is well known that NR condoms are seriously weakened when lubricated by mineral oil, petroleum jelly, and vegetable oils, as well as by some ingredients in feminine hygiene products and therapeutic creams. Occasionally, after contact with such materials, condoms will fail in use by tearing or disintegrating.

Laboratory examination gloves and surgeons' gloves are usually made from natural rubber latex. Although such gloves are sufficiently strong and durable for handling medical devices, physical contact etc., they are also readily weakened by contact with laboratory chemicals, hygiene products, dental compounds, mortuary fluids, etc. Thus, there is a significant commercial and safety incentive to produce gloves, condoms, and other elastomeric film products from a synthetic latex which would give a superior resistance to chemicals, lubricants, etc. Also, for the majority of users it is necessary to lubricate condoms. Since there is no natural rubber compatible lubricant available to the user directly, most condoms are prelubricated at the factory using specialty silicone oils, which are unavailable to the general public. By the nature of these low viscosity oils, the method of application and packaging, the condoms are themselves completely covered on the inner and outer side by the lubricant. The lubrication on the inside of the condom facilitates unwanted slippage and strain that could increase the incidence of strain-induced failure or loss of the condom during normal use.

A chemical resistant condom would allow implementation of the single sided lubrication concept using selected household lubricants, such as petroleum jelly, baby oil, etc. This could significantly reduce the condom failure rate by decreasing the actual strain experienced by a single sided lubricated condom. The decreased strain would result from the increased adhesion of the condom to the skin resulting from elimination of lubrication on the inside of the condom, while maintaining the outer lubrication layer that appears to be needed in the clinical environment.

More recently, there has been clarification of the possible serious allergic reactions of some persons caused by contact with natural rubber latex products. Protein residues in the latex products are the causative factors of these allergic reactions. Such reactions can lead to contact urticaria or systemic anaphylaxis. In other terms, persons with such allergies can experience itching, rashes, wheezing, or more severe symptoms when they use NR latex condoms or gloves. For this reason, and for other technical and economic factors, the manufacturing industry would like to develop the use of non-allergenic synthetic latex materials such as the materials disclosed in this application.

The present invention provides an elastomeric film product such as a condom of enhanced chemical resistance. Because of this improved chemical resistance, it is possible to employ lubrication systems that will reliably coat only the outside of the condom. The lubricant is added to the outside of the condom via a solvent and the coating is dried before rolling. This prevents the transfer of the lubrication system from the outside to the inside. As a number of these lubricants must be applied from non-aqueous solvent systems, only a chemically resistant condom can be employed with such lubricants.

Also, users will be able to employ nontoxic petroleum based lubricants found in their home to satisfy any additional needs for lubrication. Further, the condom provided by this invention will allow women to continue medicament-based vaginal therapy with a significantly decreased risk of condom failure that could be caused by excipient interaction with the condom.

BRIEF SUMMARY OF THE INVENTION

The invention provides a latex film product such as a prophylactic condom, a surgical glove, a medical examination glove, and the like, having improved chemical resistance, such product comprising a shaped film consisting essentially of a cured mixture of (a) a copolymer of acrylonitrile and butadiene or isoprene, and (b) a styrene-butadiene copolymer wherein said styrene-butadiene copolymer contains greater than about 50 weight percent polymerized styrene, and wherein said styrene-butadiene copolymer is employed in said film in proportions of from about one (1) to about fifteen (15) weight percent, based on weight of the copolymer of acrylonitrile and butadiene or isoprene. In a preferred embodiment, both copolymers are carboxylated in order to enhance the "green strength" of the uncured shaped film which facilitates the production of the products of the invention.

THE PRIOR ART

U.S. Pat. No. 4,955,392 discloses a prophylactic condom made of a blend of a low modulus polyolefin such as low density polyethylene and a thermoplastic elastomer, which can be, inter alia, nitrile rubber.

There are a number of publications that report on the chemical resistance of dipped latex gloves made of nitrile rubber. (Most are reinforced latex; some are made from films that are quite thick.) Illustrative is Silkowski et al., PERMEATION THROUGH FIVE COMMERCIALLY AVAILABLE GLOVE MATERIALS BY TWO PENTACHLOROPHENOL FORMULATIONS, Am. Ind. Hyg. Assoc. J. 45(8), 501–504 (1984).

DETAILED DESCRIPTION OF THE INVENTION

Figure 1:
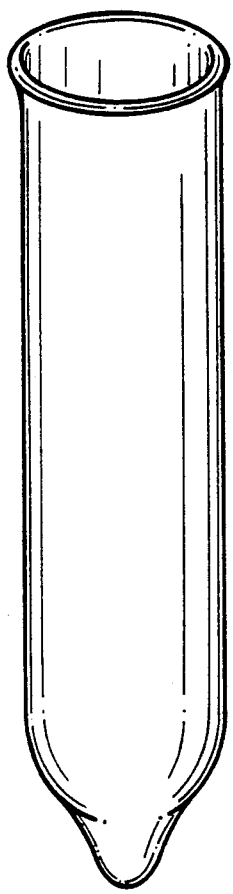
FIG. 1 shows one embodiment of the film herein shaped as a condom.

The synthetic acrylonitrile-based copolymer that is used in the invention is a latex of acrylonitrile and either butadiene or isoprene. The acrylonitrile-based copolymer is mixed with a (high-styrene) styrene-butadiene latex. Preferably, both latexes are carboxylated in order to enhance the "green strength" of the uncured film during processing.

The products such as condoms and gloves that are made from these latexes by procedures that are analogous to known commercial latex forming processes, exhibit good physical properties and excellent resistance to swelling or degradation by petroleum lubricants, petrochemical solvents, and industrial chemicals.

The synthetic acrylonitrile-based copolymer latexes that are employed in the invention, as a class, are articles of commerce. Therefore, their nature and their methods of preparation are known. The preferred acrylonitrile-based copolymer latexes contain sufficient acrylonitrile to impart the requisite chemical resistance desired for the particular application. For instance, for the production of condoms, a lower level of acrylonitrile can be used because the chemicals such as hydrocarbon lubricants and adjuvants found in vaginal medication formulations to which condoms are likely to be exposed are quite mild (even though they are powerful enough to have an adverse effect on natural rubber condoms, as is explained above). Therefore, the proportions of acrylonitrile in the latex copolymer ordinarily will be on the low side, that is, from about fifteen (15) weight percent of the latex copolymer up to about forty (40) weight percent, the remainder being isoprene or butadiene. Since medical gloves may be exposed to more powerful chemicals, a higher level of acrylonitrile is usually desired. Therefore, when the latex film product of the invention is a medical glove, acrylonitrile levels in the latex copolymer can be from about twenty (20) weight percent to about fifty-five (55) percent of the latex copolymer, the remainder being isoprene or butadiene. In some cases it is desirable to carboxylate the latex copolymer to impart improved green strength to the uncured shaped latex products. When the latex copolymer is carboxylated, usually a third monomer such as acrylic acid, methacrylic acid, or the like, is copolymerized with the acrylonitrile and the butadiene and/or isoprene. The extent of carboxylation is usually from about one (1) to about ten (10) weight percent. In this context, the percentage refers to the percent of the monomer units that contain the carboxylic acid functional group.

The high styrene styrene-butadiene latexes (the "SB latexes") used in the invention are also, as a class, known materials. Therefore their nature and methods of preparation are known. The SB latexes employed have a styrene content of greater than fifty (50) weight percent, up to, for example, about ninety (90) weight percent, and preferably from about seventy-five (75) to about eighty-five (85) weight percent, the remainder of the latex being butadiene. This latex may also be carboxylated to the extent indicated above for the acrylonitrile-containing latex in order to enhance green strength of the uncured shaped latex film product.

The SB latex is employed in an amount sufficient to enhance the tear strength of the latex film product. As a general rule, the SB latex is employed in proportions of from about 1 part to about 25 parts, and preferably from about two (2) to about fifteen (15) parts, by weight, per 100 parts of the acrylonitrile-based latex. (These proportions are on a solids basis.)

The experimental section below illustrates the methods that have been used to form latex film products of the invention.

EXPERIMENTAL

The discussion below is directed to the production of prophylactic condoms in accordance with the invention. When using the invention to produce other types of latex film products, known modifications to the process can be used. For instance, in producing surgical and medical gloves, normally only one latex dip is used, which is preceded by a dip in a coagulant (a multivalent metal salt such as calcium nitrate, calcium chloride, zinc chloride, in a suitable solvent, along with surfactants). The coagulant serves to coalesce the latex particles in a uniform manner. After the latex dip, when a coagulant is used, a leaching step is normally used to remove the coagulant salts prior to the drying/curing step.

Latex compounds were prepared in laboratory glassware and stored in sealed containers. These containers were rolled continuously to maintain good dispersion and for the appropriate time, usually 48 to 72 hours prior to dipping, to ensure maturation of the compounds.

The ingredients used are described in the listing below. The formulations in the examples are given in terms of their dry content.

Some special effort is made to obtain an appropriate viscosity of the masterbatch, by the addition of a thickening agent such as sodium polyacrylate, in order to get good wet film flow, uniform thickness, and good interlayer adhesion.

The film dipping was carried out with a 5-station laboratory dipping machine. The aluminum dipping formers are in the shape of condoms with an approximate diameter of 3.5 cm.

The formers were held stationary, and the vessels containing the latex were raised so that the formers were immersed in latex. At the beginning of the dipping sequence, the vessels containing the various latex mixtures are located on a tray mounted directly beneath the formers. The tray is hydraulically lifted at a speed of 40 cm/min, so that the formers are almost completely immersed into the latex.

In the second step, the tray is lowered at a speed of 20 cm/min until the formers are completely out of the latex. Immediately thereafter, the formers are rotated around their longitudinal axes at a speed of 10 rpm, and they are moved into a horizontal position. While rotating, they are irradiated with a Boekamp 1500 W Quartz heater (Model 1001), at a distance of 20 cm from the formers. Then the dipping and drying sequence is repeated to give a double layer of continuous rubber film. It is standard practice to use this double-dipping procedure in the production of condoms in order to insure the absence of pinholes.

The formers are removed from the dipping machine, and placed into a curing oven for 55 minutes at 100° C. After curing, the formers are taken out and cooled for 15 minutes. The film is then dusted with talc, and removed by a simple pulling action.

In commercial scale operation, it is expected that the procedures followed would be quite similar to those used commercially for producing shaped latex film products from natural rubber latex. There are some differences, however. In commercial scale operation, natural rubber latex can be "prevulcanized", that is, the latex may be subjected to elevated temperature of about 70° C. in tanks for about five hours, in order to partially cure the latex polymer to thereby shorten the time and/or lower the temperature needed for curing the shaped product. It has not been found that this can be done with the shaped latex film products of this invention. Therefore, the curing conditions of the shaped products will probably be either longer or hotter, or both, than is usually used for commercial scale production of natural rubber latex film products. It is expected, for instance, that the temperature employed in the curing tunnel section of a conventional dipping machine would be set 10° to 15° C. higher than for NR products. Also, as is done in commercial scale operations, condoms should be washed and tumble dried in a rotary drying machine for about 30 minutes at 90° C., which would complete the curing process.

MATERIALS

1. The acrylonitrile-isoprene ("A-I") latex was provided by BASF Canada Inc. The A-I latex is based on a copolymerization of 33% acrylonitrile and 67% isoprene in emulsion at low temperature using a redox catalyst system. Subsequent to polymerization it is concentrated by evaporation to higher solids content and stabilized by the addition of biocide. Some bulk properties are:

| Batch No. | P1081-½ | P1081-¾ |
| --- | --- | --- |
| Total Solids, % | 56.0 | 58.0 |
| pH | 10.6 | 10.8 |
| Viscosity, mPa | 400 | 800 |
| Surface Tension, mN/m | 42.6 | 42.6 |
| Free acrylonitrile, ppm | 35 | 14 |
| Biocide type | NaClO$_2$ | "Proxel Crl" |
| Biocide concentration, ppm | 200 | 200 |

2. BUTOFAN LATEX—Butofan LN426C is a carboxylated acrylonitrile-butadiene ("A-B") latex supplied by BASF Inc. It is a 40% solids emulsion of a carboxylated acrylonitrile-butadiene copolymer with approximately 45% bound acrylonitrile, low viscosity of 20 cps, and pH of 10.0. It contains about 5% carboxylation.

3. LATEX—Two high styrene latexes were used in the experiments. These are carboxylated styrene-butadiene copolymers which contain about 80% bound styrene, have a solids content of 50%, a pH of 9.0, and contain about 2% carboxylation:
   (i) Latex DL816 from Dow Chemical Co.
   (ii) Styronal N846 from BASF Inc.

4. KOH—Aqueous 10% solution of reagent grade Potassium Hydroxide.

5. K. Oleate—Aqueous 20% solution of potassium oleate.

6. K Laurate—20% potassium laurate solution prepared from concentrate.

7. ZDC—Zinc diethyl dithiocarbamate. This is a cure accelerator provided as a 50% aqueous emulsion.

8. TMTD—Tetramethyl thiuramdisulfide is a cure accelerator provided as a 50% aqueous emulsion.

9. ZnO—Zinc oxide is a cure activator provided as a 50% aqueous emulsion.

10. Sulfur is provided as a 65% aqueous dispersion. It acts as the primary vulcanization agent for natural rubber.

11. Wingstay L. is a proprietary antioxidant made by Goodyear Chemical Co. and provided as a 50% aqueous dispersion by General Latex and Chemicals Co.

12. Thiourea is a pure chemical compound.

13. Polyresin 5544—Sodium polyacrylate solution provided by BASF Inc. It is used as a thickener.

14. PROXEL CRL—a proprietary antibacterial compound prepared from the reaction of 4-methyl phenol with dicyclopentadiene and isobutylene, sold by ICI.

PHYSICAL PROPERTIES TESTING

The films were stripped from the formers after curing, using talc to minimize tack and self-adhesion. Test samples were cut from the rubber films using steel dies and a hydraulic press system. Physical testing was conducted at room temperature with a minimum of aging time.

TEAR STRENGTH TEST

Tear strength was evaluated using the Instron Series IX automated materials testing system, and the ASTM method D624-54. The specimens were cut using a reduced-size (but identical geometry) version of die 'C' (90° notch, 6 cm in length). The thickness (T) of each specimen at the notch was measured using a digital micrometer. The gauge or grip length (GL) was 70 mm and the crosshead speed of the Instron was 500 mm/min. The tear strength, in N/cm, was calculated from the equation F/T, wherein the maximum load (F) was measured by the Instron. The break elongation was calculated by the equation (D/GL)×100, wherein the displacement at break (D) was measured by the Instron system.

TENSILE STRENGTH TEST USING DUMBBELL-SHAPED DIE

The tensile strength of specimens was evaluated using an Instron series IX automated materials testing system. The ASTM method D412-83 was followed, using a smaller version of dumbbell die 'C' (6 cm in length). The gauge length (GL) used was 12 mm and the crosshead speed of the Instron was 100 mm/min. The thickness of each specimen was measured using a digital micrometer, and the average of three readings in the narrow region recorded. The tensile strength, in MPa, was calculated from the equation F/A, wherein the maximum load (F) was measured by the Instron and the area (A) was calculated using the width of the narrow region of the specimen and their individual thicknesses. The percent strain at break was calculated by the equation (D/GL)×100, wherein the displacement at break (D) is measured by the Instron system.

DISCUSSION OF EXAMPLES AND TEST RESULTS (i) Preparation of Condoms from Butofan A-B Latex In Table 1 the dry weight formulations of three typical Butofan latex compounds are shown. These are similar compounds wherein compounds B and C differ from compound A only by the addition of high-styrene SB latex.

Condoms were prepared by the double-dipping technique as described above, and were tested for physical properties. The average test results are shown in Table 2.

The cured double-dipped film of Butofan latex gives a very high tensile strength of 37.8 MPa (5840 psi) and moderate tear strength (the tear strength is probably lower than is desirable for commercial practice) and elongation at break.

When the film is prepared with the formulation containing 7.5 phr of SB latex, the tear strength is increased with only a slight loss in tensile strength and extensibility.

The commercial Butofan latex is supplied at a low level solids content and viscosity. This requires the use of a thickening agent in order to keep the particulate curative in suspension during the maturation and dipping operations. Since the acrylonitrile-butadiene copolymer is relatively incompatible with the sodium polyacrylic agent, there is a tendency for the latter to exude to the surface of the first dipped film. This results in difficulty in applying a second dip layer to the dried first layer.

In order to offset this effect a process was developed wherein the compound used for the first dip contains only a minimum of thickening agent. The second dip compound incorporates a higher level of thickening agent (as well as the SB copolymer latex), which results in increased viscosity of the dip and thus provides for wetting of the first film and appropriate overall product thickness. This aspect of the invention is illustrated in the tables below wherein Formulation A (acrylonitrile-butadiene latex only) was used in the first dip and Formulation C (which also contains styrene-butadiene latex) was used in the second dip.

The data of Table 2 show that this results in a film with good strength and more extensibility, as required in glove formulations.

TABLE 1

| | Dry weight Formulations | | |
|---|---|---|---|
| Compound | A | B | C |
| Butofan Latex | 100.0 | 100.0 | 100.0 |
| KOH | 0.5 | 0.5 | 0.5 |
| K Laurate | 0.06 | 0.06 | 0.5 |
| ZDC | 2.0 | 2.0 | 2.0 |
| Zn Oxide | 4.0 | 4.0 | 4.0 |
| Sulfur | 1.0 | 1.0 | 1.0 |
| Wingstay L | 1.0 | 1.0 | 1.0 |
| Latex ND846 | — | — | 12.5 |
| Latex DL816 | — | 7.5 | — |
| Polyresin | 0.2 | 0.2 | 0.3 |

TABLE 2

| Butofan Latex - Physical Properties | | | |
|---|---|---|---|
| | Formulation | | |
| Property | A | B | A + C |
| Tensile Strength (MPa) | 37.8 | 29.8 | 26.9 |
| Ultimate Elongation (%) | 470 | 445 | 525 |
| Tear Strength (N/cm) | 334 | 406 | 310 |
| Stress at 100% Strain (MPa) | 2.1 | 2.7 | 2.6 |
| Stress at 200% Strain (MPa) | 3.1 | 4.3 | 4.2 |
| Stress at 300% Strain (MPa) | 4.7 | 6.5 | 6.2 |

In pilot plant scale runs using the double dipping procedure with Formulation A as the first dip and Formulation C as the second dip, and using a slightly larger diameter former (4.0 cm vs 3.5 cm for the lab scale formers), to produce condoms, the following properties are representative of those obtained:

| Tensile strength | 35.5 MPA |
|---|---|
| Elongation at break | 560% |
| Tear strength | 330 N/cm |
| Stress at 100% | 2.2 MPa |
| Stress at 200% | 3.2 MPa |
| Stress at 300% | 5.1 MPa |

(ii) Condoms and Gloves from Acrylonitrile Isoprene Latex

The condom samples were prepared by the double dipping procedure described previously. However, the glove specimens were prepared on a ceramic glove former using the single dip/coagulant process. In this procedure the former was immersed into a proprietary coagulant solution of calcium nitrate dispersed in an aqueous ethanol solution. The salt was deposited on the former by evaporating the solvent. The salt-coated glove former was then dipped once into the latex. The latex was dried, cured at 100° C. for about one hour and then Samples of the dried rubber film were tested for physical properties and chemical resistance. Several compound formulations were investigated. Some data for these example formulations are shown in Table 3.

TABLE 3

| Formulations and Physical Properties | | | |
|---|---|---|---|
| Formulation: | D | E | F |
| Latex P1081 | 100 | 100 | 90 |
| Latex DL816 | — | — | 10 |
| KOH | 0.25 | 0.5 | 0.5 |
| K Oleate | 1 | 1 | 1 |
| Sulfur | 1 | 1 | 1.5 |
| ZDC | 1 | 1 | 1 |
| ZMBT | 2 | — | — |
| TMDT | — | 3 | 3 |
| ZnO | 3 | 4 | 3 |
| Wingstay L | 1 | 1 | 1 |
| Thiourea | — | 1 | 1 |
| Tensile Strength (MPa) | 19.0 | 24.7 | 19.8 |
| Elongation at Break (%) | 850 | 677 | 645 |
| Tear Strength (N/cm) | 183 | 204 | 262 |

In formulation D, two salt type accelerators are used to give a balance of early initiation and a sustained reaction to make use of the sulfur. These are zinc diethyldithiocarbamate (ZDC) and the zinc salt of mercaptobenzothiazole (ZMBT). The physical properties of the cured films are acceptable for gloves but perhaps a little on the low side for tensile strength and tear resistance for use in condoms.

Some earlier studies by M. W. Philpott of the Natural Rubber Producers Research Association demonstrated that some sulfur donor types of accelerators which are very sluggish at 100° C. can be activated by the addition of other sulfur bearing compounds such as thiourea.

Thus the formulation E was tested over a range of cure times and temperatures. For the typical cure of one hour at 100° C. a good level of tensile strength was obtained with an increase in tear resistance. The elongation at break is still acceptable for the manufacture of gloves. In this formulation the level of zinc oxide was increased also. The test data are more consistent with this formulation. It is known that higher levels of zinc oxide in most rubber compounds reduce the variations in cure as temperature is varied. Also any tendency to degrade is reduced.

Blends of the acrylonitrile-isoprene latex with the high-styrene carboxylated styrene-butadiene latex were prepared and gloves and condoms were dipped. As found before, and with natural rubber blends, the addition of the SB copolymer significantly increases the tear strength of the A-I films. However, there is some reduction in tensile strength and elongation at break.

General Comments

The acrylonitrile-isoprene latex, like the Butofan latex, is somewhat difficult to double dip since the surface of the dried film tends to repel a second dip. This is offset somewhat by the inclusion of the SB latex.

In contrast, the A-I latex is readily coagulant-dipped and gives a very smooth and uniform dry film by this technique.

Chemical Resistance

Condoms made from the Butofan latex as well as commercial natural rubber condoms were immersed in petroleum jelly (Vaseline) and in mineral oil for a period of 96 hours at 37° C. (body temperature). After this period of time the condoms were removed and measured for length, width and thickness.

The natural rubber condom immersed in Vaseline increased in length, width and thickness by 25% of each dimension. This corresponds to a swelling of approximately 90% increase in volume. For the natural rubber condom immersed in mineral oil there was also a consistent increase in length, width and thickness of 33% which corresponds to a volume increase of about 140%.

In contrast, there was nil increase in dimensions of the Butofan condoms in either lubricant. Sections of the gloves and condoms made from both the Butofan latex and the acrylonitrile-isoprene latex were tested for their resistance to swelling and degradation in several commercial chemical fluids. The data of Table 4 shows the degree of swelling after immersion for 24 hours at room temperature.

TABLE 4

| | % VOLUME SWELL AFTER 24 HRS AT ROOM TEMPERATURE | | |
|---|---|---|---|
| | Latex | | |
| Fluid | Natural Rubber | Butofan | A-I Latex |
| Water | <5 | <5 | <5 |
| Ethanol | <5 | 50 | 10 |
| ASTM Oil #3 (aromatic) | 270 | 2 | 5 |
| ASTM Fuel B | 370 | 55 | 60 |
| Toluene | 650 | 190 | 260 |
| Perchloroethylene | 580 | 50 | 90 |

A test run of condoms was made in production scale equipment using the double dipping technique as described above wherein the first dip contained only acrylonitrile/butadiene latex and the second dip contained the styrene/butadiene latex as well. The ingredients used in the dips are shown in Tables 5–7, below:

TABLE 5

| CURATIVES MASTERBATCH | | |
|---|---|---|
| Ingredient | Conc. % | Wet (kg) |
| Zinc Oxide | 26.55 | 21.24 |
| Vulcacit LDA (ZEDC)[1] | 13.28 | 10.62 |
| Wingstay L | 6.64 | 5.31 |
| Anchoid (nonionic soap) | 1.86 | 1.49 |
| Potassium Caseinate[2] | 9.29 | 7.47 |
| Bentone Clay | 0.27 | 0.22 |
| Water | 42.11 | 33.69 |

[1]Zinc diethyl dithiocarbamate
[2]Used as a thickener and a dispersing aid.

TABLE 6

| | First Dip | |
|---|---|---|
| Ingredient | Dry (phr) | Wet (kg) |
| Butofan Latex | 100 | 220.0 |
| KOH | 0.5 | 4.26 |
| Potassium Laurate | 0.06 | 0.25 |
| Curatives Masterbatch | 7.0 | 12.24 |
| Sulfur | 1.0 | 1.753 |
| Polyresin | 0.05 | 0.412 |

TABLE 7

| | Second Dip | |
|---|---|---|
| Ingredient | Dry (phr) | Wet (kg) |
| Butofan Latex | 100 | 220.0 |
| Styronal N846 Latex | 10 | 22.0 |
| KOH | 0.5 | 4.26 |
| Potassium Laurate | 0.5 | 2.13 |
| Curatives | 7.0 | 12.24 |
| Sulfur | 1.0 | 1.71 |
| Polyresin | 0.3 | 2.65 |

Typical properties found for these condoms made as follows:

| | Tensile Strength (MPa) | Ultimate Elongation (%) | Tear Strength (N/cm) |
|---|---|---|---|
| Average | 27.8 | 471 | 251 |
| Std. Dev'n | 3.4 | 27 | 54 |
| Minimum | 20.1 | 383 | 131 |
| Maximum | 34.2 | 533 | 378 |

What is claimed is:

1. A latex film product comprising a film shaped as a condom consisting essentially of a cured mixture of (a) a copolymer of acrylonitrile and butadiene or isoprene, and (b) a styrene-butadiene copolymer wherein said styrene-butadiene copolymer contains greater than about 50 weight percent polymerized styrene, and wherein said styrene-butadiene copolymer is employed in said film in proportions of from one to about one to about fifteen weight percent, based on weight of the copolymer of acrylonitrile and butadiene or isoprene.

2. The latex film product of claim 1 wherein the copolymer (a) is a carboxylated acrylonitrile/butadiene copolymer.

3. The latex film product of claim 1 wherein the copolymer (a) is a carboxylated acrylonitrile/isoprene copolymer.

* * * * *